(12) United States Patent
Hatanaka et al.

(10) Patent No.: US 6,640,632 B1
(45) Date of Patent: Nov. 4, 2003

(54) ULTRASONIC FLAW DETECTION METHOD AND APPARATUS

(75) Inventors: Hiroaki Hatanaka, Yokohama (JP); Saburo Shibata, Ageo (JP); Takahiro Arakawa, Yokosuka (JP)

(73) Assignee: Ishikawajima-Harima Heavy Industries Co., Ltd., Tokyo (JP)

( * ) Notice: Subject to any disclaimer, the term of this patent is extended or adjusted under 35 U.S.C. 154(b) by 0 days.

(21) Appl. No.: 10/135,307

(22) Filed: Apr. 30, 2002

(51) Int. Cl.$^7$ .......................... G01N 29/04; G01B 17/02
(52) U.S. Cl. ............................................ 73/598; 73/627
(58) Field of Search .......................... 73/596, 597, 598, 73/602, 627, 628

(56) References Cited

U.S. PATENT DOCUMENTS

| | | | | |
|---|---|---|---|---|
| 4,137,779 A | * | 2/1979 | Wustenberg et al. | 73/627 |
| 4,265,119 A | | 5/1981 | Dubetz et al. | |
| 4,406,167 A | * | 9/1983 | Maeda | 73/622 |
| 4,435,984 A | * | 3/1984 | Gruber | 73/628 |
| 4,531,409 A | | 7/1985 | Koch et al. | |
| 4,570,487 A | * | 2/1986 | Gruber | 73/624 |
| 5,515,727 A | | 5/1996 | Miwa et al. | |
| 5,646,350 A | | 7/1997 | Robinson et al. | |
| 5,801,312 A | | 9/1998 | Lorraine et al. | |
| 6,016,700 A | | 1/2000 | Cuffe | |

FOREIGN PATENT DOCUMENTS

| | | |
|---|---|---|
| EP | 0 654 666 A1 | 5/1995 |
| EP | 0 829 714 A1 | 3/1998 |
| JP | 56-147063 | 11/1981 |
| JP | 58-58463 | 4/1983 |
| JP | 59-122943 | 7/1984 |
| JP | 2-105054 | 4/1990 |
| JP | 08-211029 | 8/1996 |
| JP | 11-037982 | 2/1999 |
| WO | WO 92/08128 | 5/1992 |
| WO | WO 94/27402 | 11/1994 |
| WO | WO 97/11364 | 3/1997 |
| WO | WO 97/27477 | 7/1997 |

* cited by examiner

Primary Examiner—Richard A. Moller
(74) Attorney, Agent, or Firm—Fish & Richardson P.C.

(57) ABSTRACT

In the ultrasonic flaw detection method and apparatus, wideband longitudinal ultrasonic waves are irradiated from an ultrasonic wave generator probe onto a weld portion of a coarse grained material; from the waveforms of flaw detection echoes that are subsequently obtained, the highest frequency component that can be extracted using time frequency analysis is then extracted; subsequent ½ magnification frequency components are then extracted sequentially; waveforms of a necessary plurality of frequency bands from among each of the frequency bands that were extracted and have undergone waveform separation are then multiplied, and waveform peaks that are formed by the multiplication are detected as being defect portion echoes generated by defect portions in the coarse grained material weld portion; and, as a result, information on the defect portion is obtained from the detected defect portion echo.

4 Claims, 5 Drawing Sheets

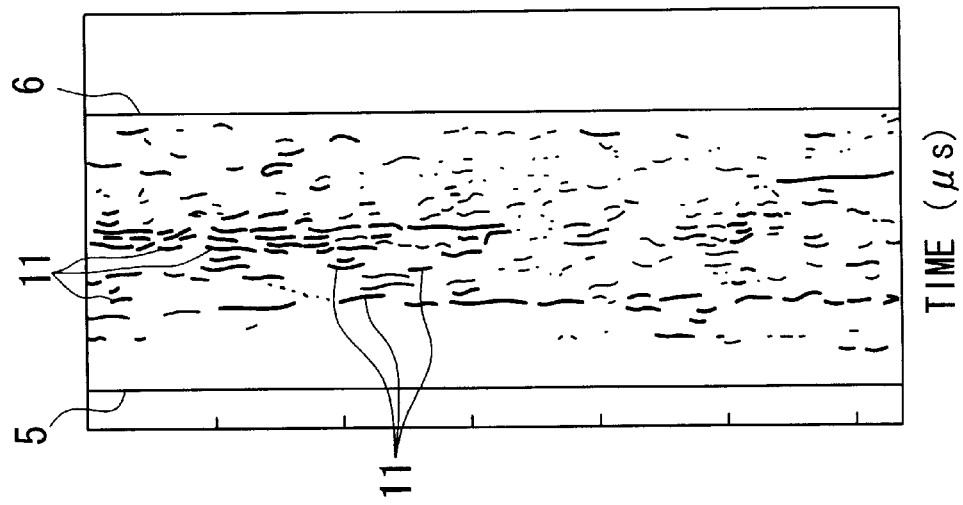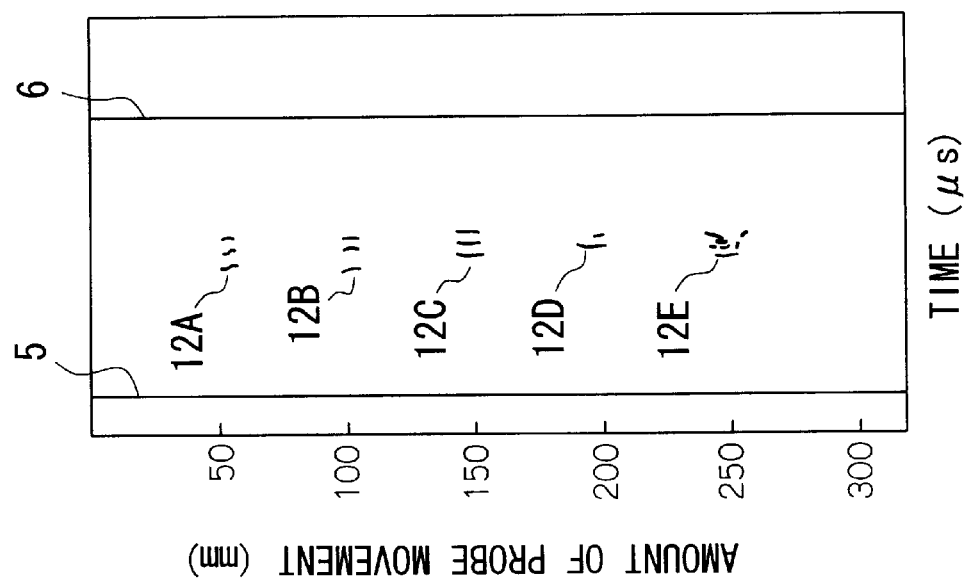

ULTRASONIC FLAW DETECTION METHOD AND APPARATUS

BACKGROUND OF THE INVENTION

1. Field of the Invention

The present invention relates to an ultrasonic flaw detection method and apparatus for detecting defect portions in weld portions of coarse grained materials (i.e. in weld portions of austenitic steel), and particularly to an ultrasonic flaw detection method an apparatus that enable echoes from a defect portion to be detected at a high S/N (Signal to Noise) ratio.

2. Description of the Related Art

One of the nondestructive inspection methods used to nondestructively inspect machinery and structures and the like in various types of industrial plants, to detect deterioration in structural materials and defects such as blowholes in welds and flaws caused by damage, to evaluate the soundness of the machinery and structures and the like, and to predict the remaining lifespan thereof is the ultrasonic flaw detection method.

In a conventional ultrasonic flaw detection method, a defect is detected when transverse ultrasonic waves are propagated through a steel structure that is being inspected, and defect echoes generated when the ultrasonic waves collide with a defect and are reflected are detected, thus providing information on the defect. An example of an ultrasonic flaw detection apparatus for use in a TOFD (Time Of Flight Diffraction) type of detection method, which is known as an excellent ultrasonic flaw detection method for obtaining sizing information as it enables information such as the position and size of a defect to be obtained, is schematically shown in FIGS. 6A to 6C. A pair formed by an ultrasonic wave generator probe 2 and an ultrasonic wave receiver probe 3 that are both connected an ultrasonic transceiver 1 are positioned in the area where a nondestructive inspection is to be performed, for example, on both sides of a weld portion (a weld bead) 4a welded in a steel material 4 such that the two probes are substantially the same distance from the weld portion 4a. Ultrasonic flaw detection echoes propagated by the ultrasonic transceiver 1 through the steel material 4 via the ultrasonic wave generator probe 2 are received by the ultrasonic transceiver 1 via the ultrasonic wave receiver probe 3.

As is shown in FIG. 6C, contained in these received ultrasonic flaw detection echoes are surface transmission waves 5 that pass from the ultrasonic wave generator probe 2 through surface portions of the steel material 4 and arrive directly at the ultrasonic wave receiver probe 3, and bottom surface reflection waves 6 that are irradiated from the ultrasonic wave generator probe 2 into the steel material 4, arrive at the bottom surface of the steel material 4 and are then reflected, and then arrive at the ultrasonic wave receiver probe 3. If there is a defect portion 7 inside the weld portion 4a on a flat plane transversing the weld portion 4a and running in a straight line between the two probes 2 and 3, a portion of the ultrasonic waves irradiated into the steel material 4 are scattered by the distal end of the defect portion 7. They are then refracted resulting in defect portion echoes (defect scatter waves) 8 that arrive at the ultrasonic wave detector 3 later than the surface transmission waves 5 and earlier than the bottom surface reflection waves 6 being contained in the ultrasonic flaw detection echoes.

Moreover, as is shown in FIG. 6A, the received ultrasonic flaw detection echoes are processed by an image processing apparatus 9 that is connected to the ultrasonic transceiver 1 while moving the two probes 2 and 3 in parallel along the weld portion 4a. An image is then displayed, for example, as is shown in FIG. 6B, by plotting XY coordinates on a monitor screen 10 taking the length of time that lapses after the transmission of ultrasonic waves from the ultrasonic wave generator probe 2 as the X axis and the amount of movement of the probes 2 and 3 as the Y axis. In this case, when the probes 2 and 3 arrive at the transverse position of the defect portion 7, defect portion echoes 8 are detected. Accordingly, by corresponding the plotted Y coordinates of the defect portion echoes 8 to the amount of movement of the probes 2 and 3, information on the position of the defect portion 7 in the direction of movement of the probes 2 and 3 can be obtained. As the probes 2 and 3 continue their movement and pass the transverse position of the defect portion 7, the defect portion echoes 8 are no longer detected. Thus, information relating to the size of the defect portion 7 in the direction of movement of the probes 2 and 3 is obtained from the amount of the movement of the probes 2 and 3 while the defect portion echoes 8 are being detected, namely, is obtained from the plotted length of the defect portion echoes 8 in the Y axis direction. Furthermore, position information relating to the depth of the defect portion 7 is obtained from the length of time that lapses after the transmission of ultrasonic waves from the ultrasonic wave generator probe 2 until the defect portion echo 8 is detected, namely, is obtained from the plotted X coordinates of the defect portion echo 8 and from the rate of ultrasonic wave propagation through the steel material 4 that has been determined in advance.

When, for example, an ultrasonic flaw detection method is used to evaluate the soundness of weld portions in coarse grained materials (austenitic steel) such as 9% nickel steel and inconel and austenitic stainless steel that are widely used in atomic plants and chemical plants, there is a sizable attenuation in the transverse ultrasonic waves and flaw detection is difficult. Therefore, ultrasonic flaw detection using longitudinal ultrasonic waves is becoming more common.

However, because columnar crystals often appear in weld portions in austenitic steel, noise echoes from the columnar crystals are often generated even when the above longitudinal ultrasonic waves are used. Moreover, because the sizes of these noise echoes are substantially the same as the sizes of the defect portion echoes generated when a defect is present in the weld portion, it is not possible to distinguish between defect portion echoes and noise echoes by simple threshold value processing. Namely, in ultrasonic flaw detection methods for coarse grained materials, the problems of a low S/N ratio in defect portion echoes and a low flaw detection performance arise.

It is an aim of the present invention to provide an ultrasonic flaw detection method and apparatus that enable defect portion echoes to be detected with a high S/N ratio from among ultrasonic flaw detection echoes from weld portions in austenitic steel.

SUMMARY OF THE INVENTION

During repeated research into ways of improving S/N ratios in ultrasonic flaw detection performed on weld portions in austenitic steel, the present inventors noticed that because the noise echoes are reflection waves from grain boundaries and are formed by waves from countless reflection sources mutually interfering with each other, if waveforms obtained as ultrasonic flaw detection echoes are separated into the necessary frequency components (frequency bands), the waveform phase (the peak emergence position relative to the time axis) is different for each frequency band. The present inventors also noticed that, in contrast to this, in defect portion echoes, the waveforms all have the same phase even if the frequency bands are different, namely, the positions of peak emergence relative to the time axis all match. As a result, the present inventors discovered that by separating original waveforms of ultrasonic flaw detection echoes into the necessary frequency bands and then detecting peaks that have matching phases even though the frequency bands are different, it is possible to extract and thus detect only the peaks of defect portions, and thus the present inventors achieved the present invention.

Namely, in the ultrasonic flaw detection method and apparatus of the present invention: wideband longitudinal ultrasonic waves are irradiated from an ultrasonic wave generator probe onto a weld portion of a coarse grained material; from the waveforms of flaw detection echoes that are subsequently obtained, the highest frequency component that can be extracted using time frequency analysis is then extracted; subsequent ½ magnification frequency components are then extracted sequentially; waveforms of a necessary plurality of frequency bands from among each of the frequency bands that were extracted and have undergone waveform separation are then multiplied, and waveform peaks that are formed by the multiplication are detected as being defect portion echoes generated by defect portions in the coarse grained material weld portion; and, as a result, information on the defect portion is obtained from the detected defect portion echo.

Because the noise echoes are reflection waves from grain boundaries and are formed by waves from countless reflection sources mutually interfering with each other, if the highest frequency component that can be extracted using time frequency is extrated from the waveform of ultrasonic flaw detection echoes from coarse gained material weld portions and then subsaquent ½ magnification frequency components are extracted sequetially, then the waveform phase (the peak emergence position relative to the time axis) is different for each frequency band. In contrast to this, in the TOFD flaw detection method, scatterd waves from the tip end of the defect portion which are propagated as spherical waves are detected, and therefore, in defect portion echoes, the waveforms all have the same phase even if the frequency bands are different, and the positions of peak emergence relative to the time axis all match. As a result, if waveforms of the necessary frequency band components that have been extrated from the waveforms of ultrasonic flaw detection echoes and have undergone waveform seperation are multiplied, then while the noise echoes, whose phases do not match, are close to zero, defect portion echoes, whose phases do match, are amplified and form peaks. Accordingly, by detecting these peaks, the defect portion echoes can be extracted at a high S/N ratio.

Thus, according to the ultrasonic flaw detection method and apparatus of the present invention, the excellent effect of the accurate performing of ultrasonic flaw detection becoming possible is obtained.

Furthermore, in the ultrasonic flaw detection method and apparatus of the present invention: an ultrasonic wave generator probe for generating wideband longitudinal ultrasonic waves and an ultrasonic wave receiver probe are disposed symmetrically at positions on both sides of the coarse grained material weld portion; wideband longitudinal ultrasonic waves are irradiated from the ultrasonic wave generator probe onto the coarse grained material weld portion; from waveforms of flaw detection echoes that are subsequently obtained, the highest frequency component that can be extracted using time frequency analysis is then extracted; subsequent ½ magnification frequency components are then extracted sequentially; waveforms of a necessary plurality of frequency bands from among each of the frequency bands that were extracted and have undergone waveform separation are then multiplied, and waveform peaks that are formed by the multiplication are detected as being defect portion echoes generated by defect portions in the coarse grained material weld portion; and position information and size information about the defect portion are obtained by displaying the detected defect portion echoes as an image by plotting them on XY coordinates that take an amount of movement of the probes as one axis and a length of time lapsed from a transmission of an ultrasonic wave by the ultrasonic wave generator probe as another axis.

In this case, it is possible obtain accurate position information about a defect portion in the direction of movement of the probes from the amount the probes move after the detection of the defect portion echo commences based on a defect echo portion detected at a high S/N ratio when noise echoes have been separated and removed. In addition, accurate information about the size of the defect portion in the direction of movement of the probes can be obtained from the amount the probes move from the start of the detection of the defect portion echoes until the end of the detection thereof. Furthermore, accurate position information about the depth of the defect portion can be obtained based on the time the defect portion echoes are detected and the transmission speed of ultrasonic waves inside the coarse grained material, which is determined in advance.

The result of this is that the accuracy of detecting defect portions is improved. In cases, particularly, when this ultrasonic flaw detection method and apparatus are used in non-destructive inspections of an existing plant, the remaining lifespan diagnosis of the plant can be made with a high degree of accuracy.

BRIEF DESCRIPTION OF THE DRAWINGS

FIG. 5A is a view showing a result of an ultrasonic flaw detection test when the apparatus shown in FIG. 1 is used.

FIG. 5B is a showing a result of an ultrasonic flaw detection test when analysis of the ultrasonic flaw detection echo is not performed.

DESCRIPTION OF THE PREFERRED EMBODIMENTS

A preferred embodiment of the present invention will now be described with reference made to the drawings.

Figure 1A:
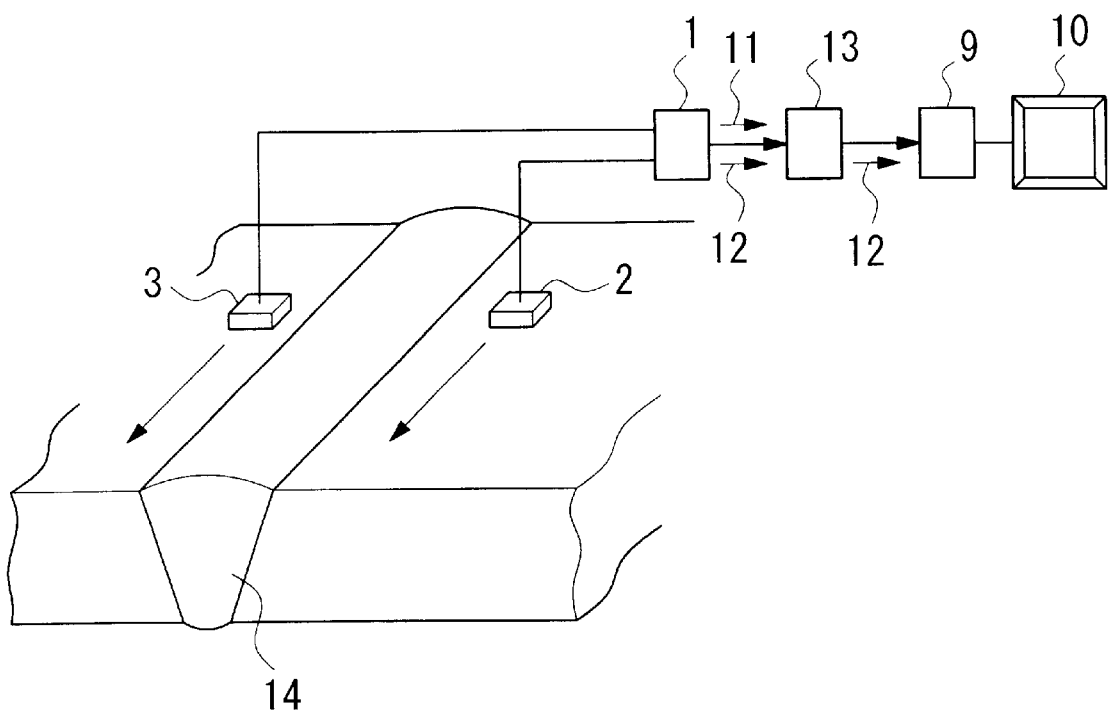
FIG. 1A is a schematic perspective view showing an embodiment of the ultrasonic flaw detection method and apparatus of the present invention.
Figure 1B:
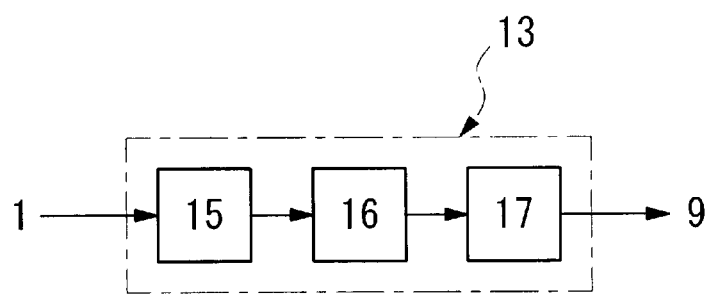
FIG. 1B is a detailed view of a waveform analyzer showing an embodiment of the ultrasonic flaw detection method and apparatus of the present invention.
Figure 6A:
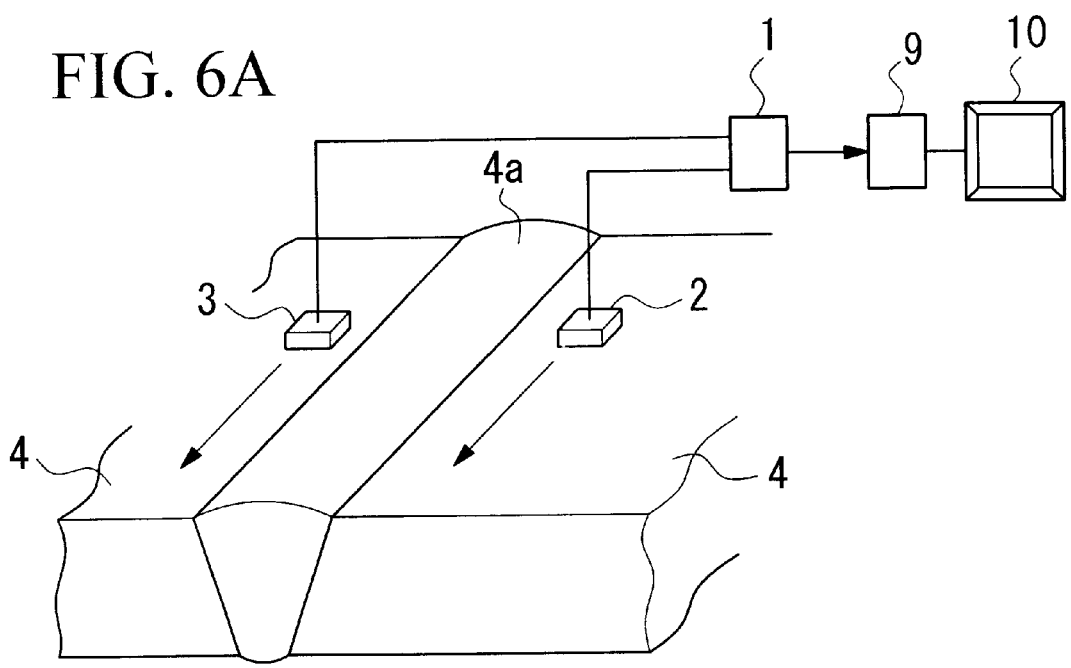
FIG. 6A is a perspective view schematically showing an example of a conventional TOFD type of ultrasonic flaw detection apparatus.
Figure 6B:
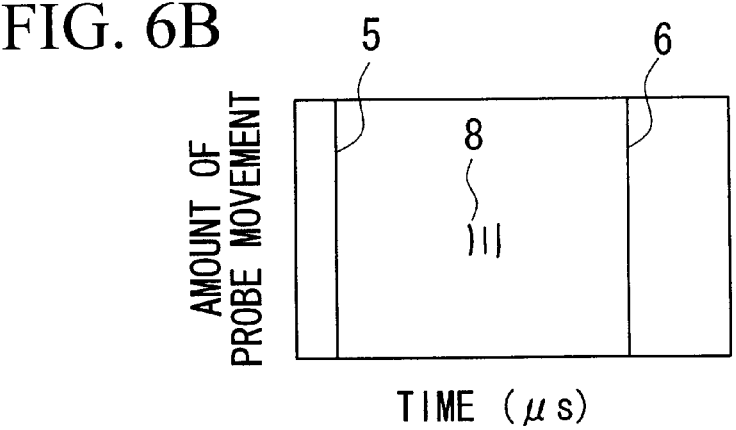
FIG. 6B is an enlarged view of a monitor screen schematically showing an example of a conventional TOFD type of ultrasonic flaw detection apparatus.
Figure 6C:
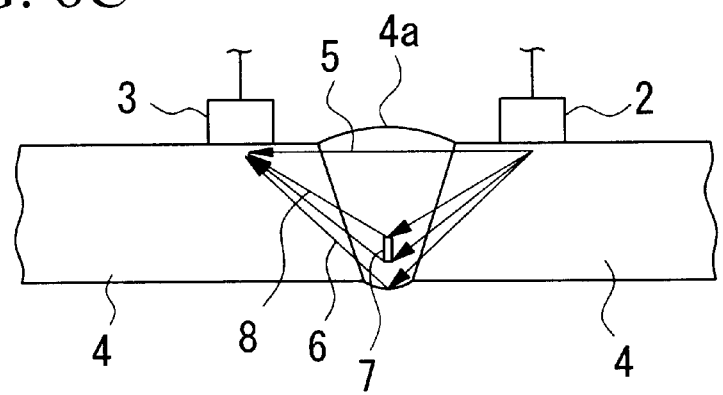
FIG. 6C is a typical view showing an example of the transmission path of an ultrasonic flaw detection echo in a conventional TOFD type of ultrasonic flaw detection apparatus.

An embodiment of the ultrasonic flaw detection method and apparatus of the present invention is shown in FIGS. 1A and 1B. In this flaw detection apparatus, in the same TOFD type of ultrasonic flaw detection apparatus as is shown in FIGS. 6A to 6C, the ultrasonic wave generator probe 2 is formed by an ultrasonic wave generator probe 2 that is capable of transmitting longitudinal ultrasonic waves over a wide band centered on 2 MHz. In addition, between the ultrasonic transceiver 1 and the image processing apparatus 9 is provided a waveform analyzer 13 that analyzes ultrasonic flaw detection echoes detected by the ultrasonic transceiver 1 and extracts defect portion echoes 12 at a high S/N ratio.

As is shown in detail in FIG. 1B, the waveform analyzer 13 is formed by a wavelet analyzing section 15, a storage section 16, and a calculation section 17. The wavelet analyzing section 15 serves as an analyzing section for performing waveform separation by extracting the highest frequency components that can be extracted using time frequency analysis, for example, the component in the 10 MHz frequency band, from the waveform of flaw detection echoes sent from the ultrasonic transceiver 1, and then extracting subsequent ½ magnification frequency components in sequence. The storage section 16 stores the waveforms of the components of each frequency band on which the wavelet analyzing section 15 has performed waveform separation. The calculation section 17 multiplies waveforms of a required plurality of frequency bands from among the waveforms of the respective frequency bands stored in the storage section 16, and detects peaks forming in the waveforms as being defect portion echoes 12 generated by a defect portion 7 in a coarse grained material weld portion 14, and then outputs these to the image processing apparatus 9.

In the same way as a conventional image processing apparatus 9, the image processing apparatus 9 displays the signals of the defect portion echoes 12 sent from the waveform analyzer 13 as XY coordinates on a monitor screen 10, taking the amount of movement of the probes as the X axis and the length of time that lapses after the transmission of ultrasonic waves from the ultrasonic wave generator probe 2 as the Y axis. Apart from these, those members that are the same as members shown in FIGS. 6A to 6C are given the same descriptive symbols as in FIGS. 6A to 6C.

When performing flaw detection on the coarse grained material weld portion 14, in the same way as when performing conventional flaw detection on the weld portion 4a of a steel material, firstly, the ultrasonic wave generator probe 2 and the ultrasonic wave receiver probe 3 are disposed substantially symmetrically at positions on both sides of the coarse grained material weld portion 14. Next, longitudinal ultrasonic waves are transmitted from the ultrasonic transceiver 1 to the coarse grained material weld portion 14 via the ultrasonic wave generator probe 2, and the ultrasonic flaw detection echoes that are obtained are subsequently received in the ultrasonic transceiver 1 via the ultrasonic wave receiver probe 3. The ultrasonic flaw detection echoes that are received are then analyzed by the waveform analyzer 13 and defect portion echoes 12 are separated from noise echoes 11 and then extracted. Thereafter, the detected and extracted defect portion echoes 12 are sent to the image processing apparatus 13 and displayed as XY coordinates on the monitor screen 10.

Here, the principle of the analysis processing by the waveform analyzer 13 will be described using FIGS. 2A to 2M and FIG. 3.

The analysis method (waveform separation analysis method) used for performing time frequency analysis allows frequency analysis of the waveform to be performed without any information on the time axis of the waveform being lost. Each of the waveform frequency analyses shown below is performed using this waveform separation analysis method.

Figure 2A:
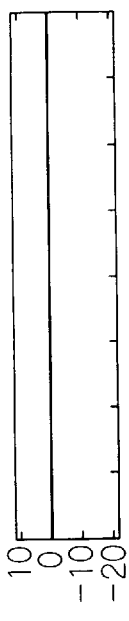
FIG. 2A is a view for explaining the principle of the time frequency analysis of the waveform analyzer in the apparatus in FIG. 1 and shows an original waveform of an ultrasonic flaw detection echo.
Figure 2C:
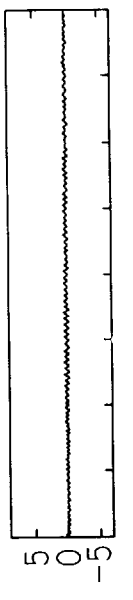
FIG. 2C is a view for explaining the principle of the time frequency analysis of the waveform analyzer in the apparatus in FIG. 1 and shows a waveform remaining after the extraction of the waveform of a particular frequency component.
Figure 2E:
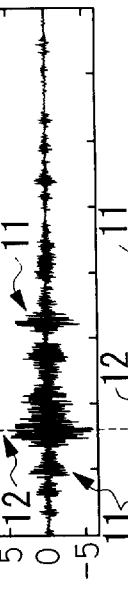
FIG. 2E is a view for explaining the principle of the time frequency analysis of the waveform analyzer in the apparatus in FIG. 1 and shows a waveform remaining after the extraction of the waveform of a particular frequency component.
Figure 2G:
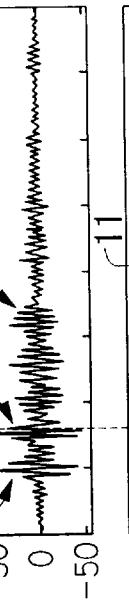
FIG. 2G is a view for explaining the principle of the time frequency analysis of the waveform analyzer in the apparatus in FIG. 1 and shows a waveform remaining after the extraction of the waveform of a particular frequency component.
Figure 2I:
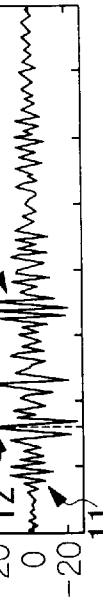
FIG. 2I is a view for explaining the principle of the time frequency analysis of the waveform analyzer in the apparatus in FIG. 1 and shows a waveform remaining after the extraction of the waveform of a particular frequency component.
Figure 2K:
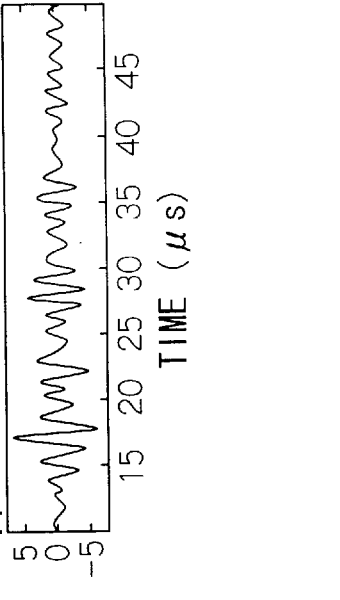
FIG. 2K is a view for explaining the principle of the time frequency analysis of the waveform analyzer in the apparatus in FIG. 1 and shows a waveform remaining after the extraction of the waveform of a particular frequency component.
Figure 2M:
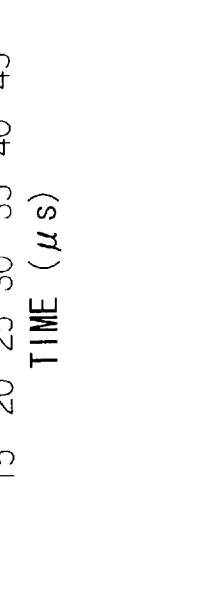
FIG. 2M is a view for explaining the principle of the time frequency analysis of the waveform analyzer in the apparatus in FIG. 1 and shows a waveform remaining after the extraction of the waveform of a particular frequency component.
Figure 2B:
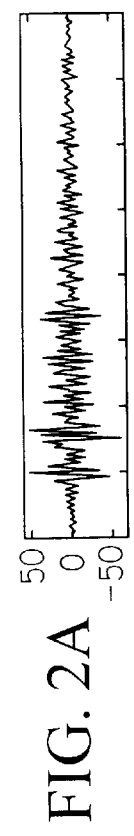
FIG. 2B is a view for explaining the principle of the time frequency analysis of the waveform analyzer in the apparatus in FIG. 1 and shows a waveform extracted as a component of a particular frequency band.

When analyzing, for example, based on Daubedries wavelet of order 10 using the wavelet analyzing section 15 an original waveform running along a time axis of an ultrasonic flaw detection echo, as is shown in FIG. 2A, that was obtained by irradiating longitudinal ultrasonic waves onto the coarse grained material weld portion 14, firstly, only, for example, the 10 MHz frequency band component undergoes waveform separation as being the highest frequency band component to be separated from the waveform, and this component is extracted as a waveform running along a time axis, such as that shown in FIG. 2B, and is stored in the storage section 16. Next, from the waveform of the ultrasonic flaw detection echoes after the 10 MHz frequency band component has been extracted, separated, and removed, such as that shown in FIG. 2C, as the next highest frequency band component, the ½ magnification frequency component of the separated frequency band is extracted as a waveform running along a time axis, such as that shown in FIG. 2B, and is stored in the storage section 16.

Figure 2D:
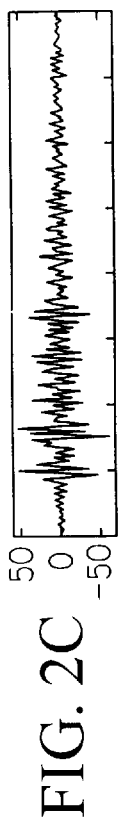
FIG. 2D is a view for explaining the principle of the time frequency analysis of the waveform analyzer in the apparatus in FIG. 1 and shows a waveform extracted as a component of a particular frequency band.
Figure 2F:
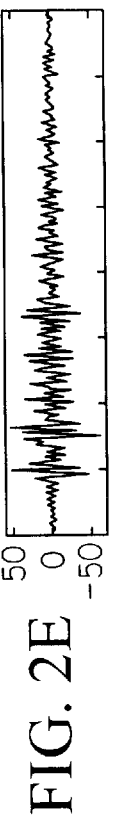
FIG. 2F is a view for explaining the principle of the time frequency analysis of the waveform analyzer in the apparatus in FIG. 1 and shows a waveform extracted as a component of a particular frequency band.
Figure 2H:
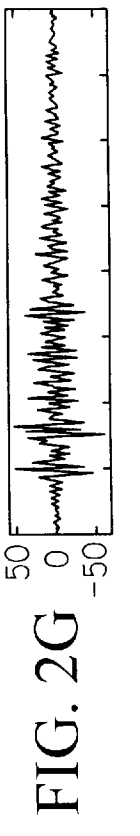
FIG. 2H is a view for explaining the principle of the time frequency analysis of the waveform analyzer in the apparatus in FIG. 1 and shows a waveform extracted as a component of a particular frequency band.
Figure 2J:
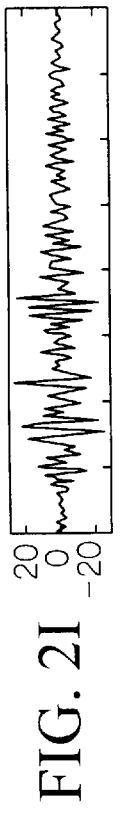
FIG. 2J is a view for explaining the principle of the time frequency analysis of the waveform analyzer in the apparatus in FIG. 1 and shows a waveform extracted as a component of a particular frequency band.
Figure 2L:
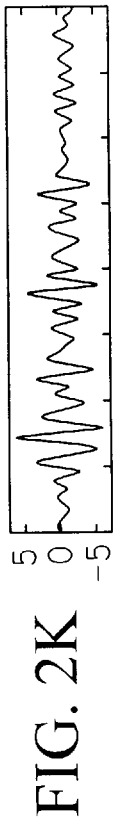
FIG. 2L is a view for explaining the principle of the time frequency analysis of the waveform analyzer in the apparatus in FIG. 1 and shows a waveform extracted as a component of a particular frequency band.

Next, from the ultrasonic flaw detection echoes remaining after the frequency band component shown in FIG. 2D has been separated and removed, such as is shown in FIG. 2E, the frequency component of a further ½ magnification frequency band, namely, the frequency component of ¼ magnification of the highest frequency band component is extracted as a waveform running along a time axis, such as that shown in FIG. 2F, and stored in the storage section 16. In the same way, from the ultrasonic flaw detection echoes remaining after the extraction, such as that shown in FIG. 2G, the waveform of the frequency component of ⅛ magnification of the highest frequency band is extracted, as is shown in FIG. 2H. Thereafter, from the ultrasonic flaw detection echoes remaining after the extraction, such as that shown in FIG. 2I, the waveform of the frequency component of ¹⁄₁₆ magnification of the highest frequency band is extracted, as is shown in FIG. 2J. Further, from the ultrasonic flaw detection echoes remaining after the extraction, such as that shown in FIG. 2K, the waveform of the frequency component of ¹⁄₃₂ magnification of the highest frequency band is extracted, as is shown in FIG. 2L. Each of these extracted waveforms is stored in the storage section 16. Note that the waveform shown in FIG. 2M is for the ultrasonic flaw detection echoes remaining after the extraction and separation of the frequency component shown in FIG. 2L.

Because the noise echoes 11 are reflection waves from grain boundaries and are formed by waves from countless reflection sources mutually interfering with each other, the waveform phase (the peak emergence position relative to the time axis) is different for each frequency band. In contrast to this, because the defect portion echoes 12 are generated when ultrasonic waves transmitted to a weld portion in a coarse grained material arrive at a defect portion and are diffracted by the defect portion, they all travel the same distance even in the case of ultrasonic waves of different frequency bands. As a result, even if the defect portion echoes 12 are separated into components of different frequency bands, the waveforms all have the same phase and the peak emergence times all match.

Figure 3:
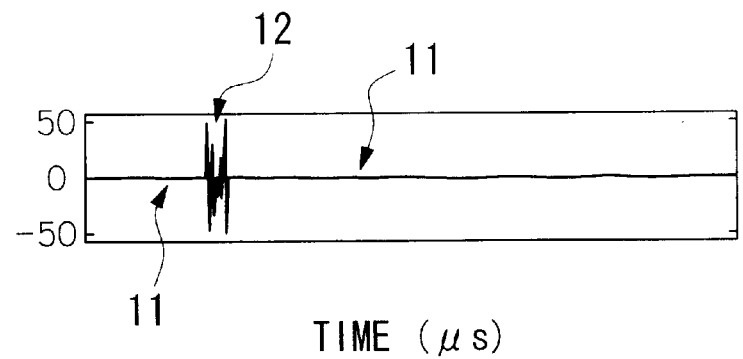
FIG. 3 is a view showing a waveform formed by the multiplication of waveforms of different frequency bands by the calculation section of the waveform analyzer in the apparatus shown in FIG. 1.

In the present embodiment, out of the wavelengths of components of the respective frequency bands stored in the storage section 16, the waveforms of components of a plurality of frequency bands from which waveforms having an intensity of approximately ⅓ that of the peak can be obtained, for example, the frequency bands shown in FIGS. 2F, 2H, and 2J are selected and are multiplied in the calculation section 17. Consequently, as is shown in FIG. 3, in the case of the noise echoes 11, because waveforms having different phases are multiplied together and the frequency bands are changed by ½ magnification steps, the components of the high frequency bands are affected, and in the waveforms generated by the above multiplication the amplitude is close to zero. In the case of the defect portion echoes 12, on the other hand, because same phase waveforms are multiplied, there is a large amplification and in the waveforms generated by the above multiplication the amplitude becomes large. As a result, it is possible to remove the noise echoes 11 and specify the waveform peaks formed by the multiplication of the waveforms of the components of the frequency bands shown in FIGS. 2F, 2H, and 2J as being the defect portion echoes 12. Thus, it is possible to extract and detect defect portion echoes 12 at a high S/N ratio from ultrasonic flaw detection echoes from a coarse grained weld portion 14 in which even when the weld is a sound one a large number of noise echoes 11 are contained.

Furthermore, because it is possible to remove the noise echoes 11 and detect the defect portion echoes 12 at a high S/N ratio, as is also made clear from the experiment results shown in FIG. 5A (described below), it is possible to plot precisely the detected defect portion echoes 12 on the monitor screen 10 without this being hindered by the noise echoes 11. As a result, it is possible to accurately obtain information about the defect portion 7 in the direction of movement of the probes 2 and 3 from the amount of the movement of the probes 2 and 3 when the defect portion echoes 12 begin to be detected position. In addition, it is possible to accurately obtain information about the size of the defect portion 7 in the direction of movement of the probes 2 and 3 from the amount of the movement of the probes 2 and 3 when the defect portion echoes 12 begin to be detected. Furthermore, based on the time when the defect portion echo 12 is detected and the transmission speed of the ultrasonic waves inside coarse grained material (which is determined in advance), it is possible to obtain accurate position information concerning the depth of the defect portion 7. As a result, the accuracy of defect portion detection is improved, and in particular, when this ultrasonic flaw detection method and apparatus are used in a nondestructive inspection of an existing plant, the remaining lifespan diagnosis of the plant can be made with a high degree of accuracy.

Moreover, because the defect portion echoes 12 are scattered waves that are scattered by a distal end of the defect portion 7 portion in the coarse grained material weld portion 14, even if the defect portion echoes 12 are echoes from an irregularly shaped defect portion 7, it is possible to eliminate the possibility of wave interference being generated, thereby allowing the detection accuracy to be further improved.

EXAMPLES

A description will now be given of the results of examples carried out by the present inventors with the aim of demonstrating the effects of the present invention.

Figure 4A:
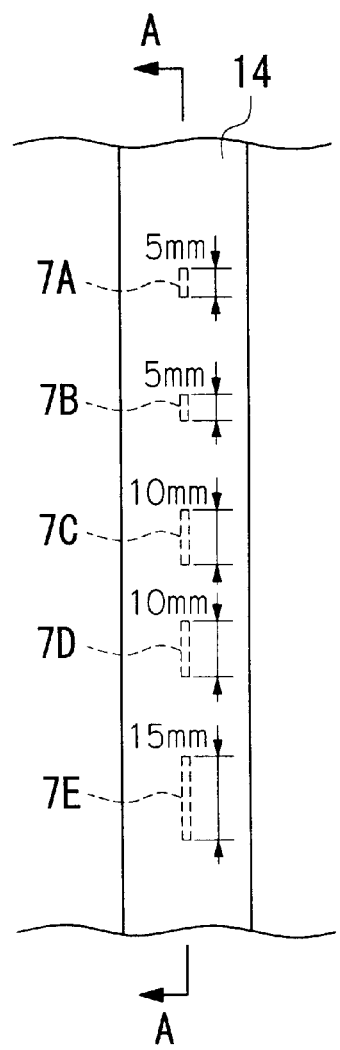
FIG. 4A is a schematic plan view showing samples of coarse grained material weld portions used in tests of the ultrasonic flaw detector using the apparatus shown in FIG. 1.
Figure 4B:
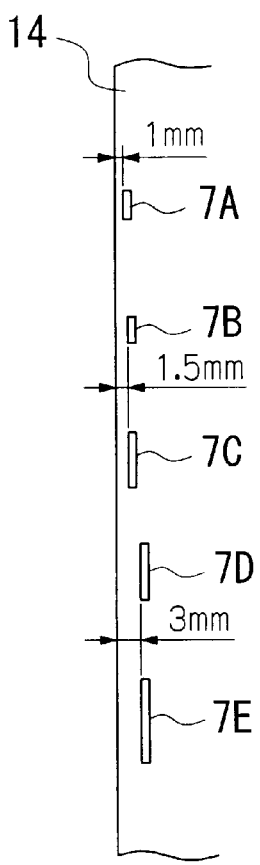
FIG. 4B is a view taken along the line A—A in FIG. 1 showing samples of coarse grained material weld portions used in tests of the ultrasonic flaw detector using the apparatus shown in FIG. 1.

As is shown in FIGS. 4A and 4B, ultrasonic flaw detection was performed using the ultrasonic flaw detection apparatus of the present invention shown in FIGS. 1A and 1B on a test piece in which defect portions 7A, 7B, 7C, 7D, and 7E in which incomplete fusion was simulated were formed in 9% NI steel weld portions serving as coarse grained material weld portions 14. The results of this ultrasonic flaw detection were compared with the results obtained when a conventional TOFD type of ultrasonic flaw detection apparatus such as that shown in FIGS. 6A to 6C was used. The defect portion 7A has a width of 5 mm and a depth of 1 mm in the direction of movement of the probes 2 and 3. In the same way, the defect portion 7B has a width of 5 mm and a depth of 1.5 mm, the defect portion 7C has a width of 10 mm and a depth of 1.5 mm, the defect portion 7D has a width of 10 mm and a depth of 3 mm, and the defect portion 7E has a width of 15 mm and a depth of 3 mm.

The results of the comparison are shown in FIGS. 5A and 5B. FIG. 5A shows the results of the ultrasonic flaw detection test using the ultrasonic flaw detection apparatus of the present invention. The defect portion echoes 12A, 12B, 12C, 12D, and 12E that correspond respectively to the defect portions 7A, 7B, 7C, 7D, and 7E were accurately detected on the monitor screen 10 without any interference from the noise echoes 11. In this case, each of the defect portion echoes 12A, 12B, 12C, 12D, and 12E is plotted on a Y coordinate corresponding to the position in the movement direction of the probes 2 and 3 of the corresponding defect portion 7A, 7B, 7C, 7D, and 7E. Moreover, it was determined that the respective lengths thereof in the Y axis direction correspond to the widths in the movement direction of the probes 2 and 3 of the respective defect portions 7A, 7B, 7C, 7D, and 7E. Furthermore, there was a greater delay in the detection time of the defect portion echoes 12C and 12D than in the detection time of the defect portion echoes 12A and 12B, while there was a still greater delay until the defect portion echo 12E was detected. Therefore, it was determined that the value of the X coordinate of the respective defect portion echoes 12A, 12B, 12C, 12D, and 12E reflects position information relating to the depth of the respective defect portions 7A, 7B, 7C, 7D, and 7E. Accordingly, according to the ultrasonic flaw detection apparatus of the present invention, it is possible to detect each of the defect portions 7A, 7B, 7C, 7D, and 7E with a high degree of accuracy.

In contrast to this, in the flaw detection results obtained using the conventional ultrasonic flaw detection apparatus shown in FIG. 5B, it is clear that because a large number of noise echoes emerge, the defect portion echoes 12A, 12B, 12C, 12D, and 12E are difficult to pinpoint, so that, as a result, the defect portions 7A, 7B, 7C, 7D, and 7E cannot be detected.

It is to be understood that the present invention is not limited solely to the above described embodiment and provided that a structure is employed in which there is provided an ultrasonic wave generator probe for generating ultrasonic waves over a wide band, and in which the highest frequency components that can be extracted using time frequency analysis are extracted from the waveforms of ultrasonic flaw detection echoes generated by the ultrasonic wave generator probe, and then waveform separation is performed by extracting ½ magnification frequency components in sequence, and thereafter peaks that are formed when waveforms of a required plurality of frequency band components are multiplied are pinpointed and detected as being defect portion echoes, then it is possible for the ultrasonic flaw detection method and apparatus of the present invention to be used in a method other than a TOFD detection method such as that shown in FIGS. 1A and 1B, such as in a method that employs a single probe for both generating and receiving ultrasonic waves. Furthermore, the ultrasonic flaw detection method and apparatus of the present invention can be used in an immersion ultrasonic flaw detection, or in another flaw detection methods in which the defect portion echoes are provided as spherical waves from point sources such as an AE (acoustic emission) testing for structures. That is, in the AE testing, the defect portion echoes are provided as spherical waves from point sources, and therefore, echoes of outer noises such as the wind can be separated and removed. Furthermore, various alternatives may be employed insofar as they do not depart from the purpose of the present invention.

What is claimed is:

1. An ultrasonic flaw detection method in which:

wideband longitudinal ultrasonic waves are irradiated from an ultrasonic wave generator probe onto a weld portion of a coarse grained material;

from waveforms of flaw detection echoes that are subsequently obtained, the highest frequency component that can be extracted using time frequency analysis is then extracted;

subsequent ½ magnification frequency components are then extracted sequentially;

waveforms of a necessary plurality of frequency bands from among each of the frequency bands that were extracted and have undergone waveform separation are then multiplied, and waveform peaks that are formed by the multiplication are detected as being defect portion echoes generated by defect portions in the coarse grained material weld portion; and information on the defect portion is obtained from the detected defect portion echo.

2. A flaw detection method in which:

an ultrasonic wave generator probe for generating wideband longitudinal ultrasonic waves and an ultrasonic wave receiver probe are disposed symmetrically at positions on both sides of the coarse grained material weld portion;

wideband longitudinal ultrasonic waves are irradiated from the ultrasonic wave generator probe onto the coarse grained material weld portion while the respective probes are moved in parallel along the coarse grained material weld portion;

from waveforms of flaw detection echoes that are subsequently obtained, the highest frequency component that can be extracted using time frequency analysis is then extracted;

subsequent ½ magnification frequency components are then extracted sequentially;

waveforms of a necessary plurality of frequency bands from among each of the frequency bands that were extracted and have undergone waveform separation are then multiplied, and waveform peaks that are formed by the multiplication are detected as being defect portion echoes generated by defect portions in the coarse grained material weld portion; and position information and size information about the defect portion are obtained by displaying the detected defect portion echoes as an image by plotting them on XY coordinates that take an amount of movement of the probes as one axis and a length of time lapsed from a transmission of an ultrasonic wave by the ultrasonic wave generator probe as another axis.

3. An ultrasonic flaw detection apparatus comprising:

an ultrasonic wave generator probe for generating wideband longitudinal ultrasonic waves;

an analysis section for extracting the highest frequency component that can be extracted using time frequency analysis from waveforms of flaw detection echoes of ultrasonic waves that are irradiated from the ultrasonic wave generator probe onto a weld portion of a coarse grained material and thereafter extracting in sequence subsequent ½ magnification frequency components;

a storage section for temporarily storing waveforms of each of the frequency bands that have been extracted and then undergone waveform separation in the analysis section; and a waveform analyzer having a calculation section that multiplies waveforms of a necessary plurality of frequency bands from among each of the frequency bands stored in the storage section, and detects waveform peaks that are formed by the multiplication as being defect portion echoes generated by defect portions in the coarse grained material weld portion.

4. An ultrasonic flaw detection apparatus comprising:

an ultrasonic wave generator probe for generating wideband longitudinal ultrasonic waves;

an ultrasonic wave receiver probe;

an analysis section for extracting the highest frequency component that can be extracted using time frequency analysis from waveforms of flaw detection echoes of ultrasonic waves that are irradiated from the ultrasonic wave generator probe onto a weld portion of a coarse grained material and received by the ultrasonic wave receiver probe, and thereafter extracting in sequence subsequent ½ magnification frequency components;

a storage section for temporarily storing waveforms of each of the frequency bands that have been extracted and then undergone waveform separation in the analysis section;

a waveform analyzer that multiplies waveforms of a necessary plurality of frequency bands from among each of the frequency bands stored in the storage section, and detects waveform peaks that are formed by the multiplication as being defect portion echoes generated by defect portions in the coarse grained material weld portion; and an image processing apparatus that, when the respective probes are moved in parallel along the coarse grained material weld portion, displays the defect portion echoes detected by the waveform analyzer as an image on a monitor screen by plotting them on XY coordinates that take an amount of movement of the probes as one axis and a length of time lapsed from a transmission of an ultrasonic wave by the ultrasonic wave generator probe as another axis.

* * * * *